United States Patent [19]

Leibinsohn

[11] 4,176,683

[45] Dec. 4, 1979

[54] FLOW REGULATOR

[75] Inventor: Saul H. Leibinsohn, Rishon-Le-Zion, Israel

[73] Assignee: Koninklijke Emballage Industrie Van Leer B. V., Amstelveen, Netherlands

[21] Appl. No.: 839,303

[22] Filed: Oct. 4, 1977

[30] Foreign Application Priority Data

Oct. 8, 1976 [NL] Netherlands .......................... 7611187
Aug. 17, 1977 [NL] Netherlands .......................... 7709108

[51] Int. Cl.² .......................... F16K 7/04; F16K 47/12
[52] U.S. Cl. .......................... 137/559; 251/4; 251/121; 251/126; 138/43
[58] Field of Search .......................... 251/126, 4, 118, 340, 251/121; 138/42, 43; 137/559

[56] References Cited

U.S. PATENT DOCUMENTS

| 2,706,101 | 4/1955 | Cantor | 251/4 |
|---|---|---|---|
| 3,254,869 | 6/1966 | Easey | 251/4 |
| 3,626,959 | 12/1971 | Santomieri | 137/1 |
| 3,785,616 | 1/1974 | Moore | 138/43 X |
| 3,841,354 | 10/1974 | McDonnell | 138/43 |
| 3,851,668 | 12/1974 | Benjamin | 137/625.3 |

FOREIGN PATENT DOCUMENTS 1011887  4/1952  France .......................... 251/4

*Primary Examiner*—Arnold Rosenthal
*Attorney, Agent, or Firm*—Stevens, Davis, Miller & Mosher

[57] ABSTRACT

A presettable fluid flow regulator having a body in the form of an elongated sleeve of flexible material and a core within the sleeve having a recess of varying cross section on its outer surface along its length. A ring on the outside of the sleeve having an internal diameter slightly less than the outer diameter of the sleeve is used to squeeze the sleeve against the core to define a flow passage between the body and the sleeve. The volume of flow is determined by the longitudinal position of the ring along the sleeve.

18 Claims, 11 Drawing Figures

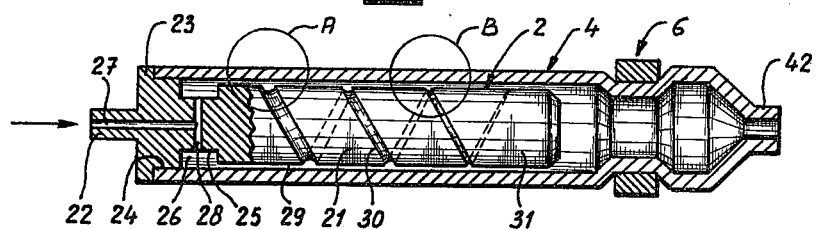
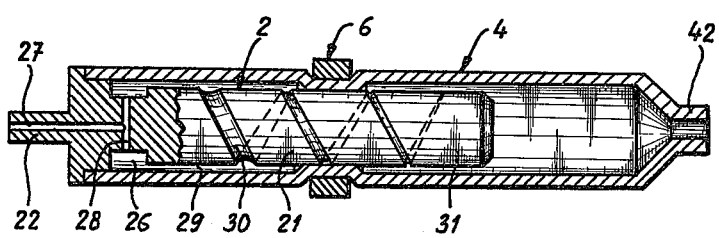
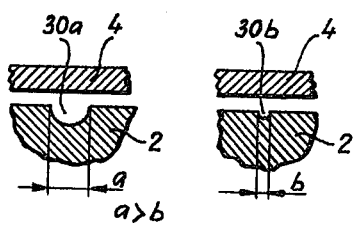
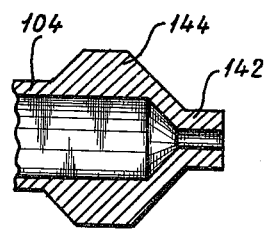
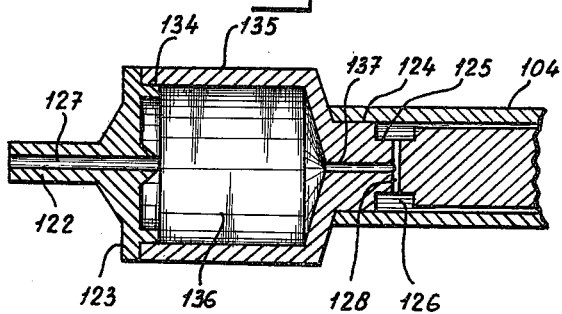
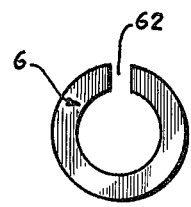

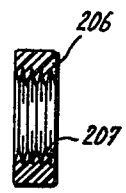
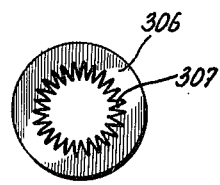
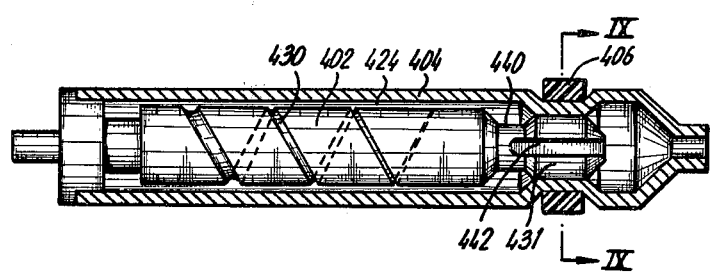
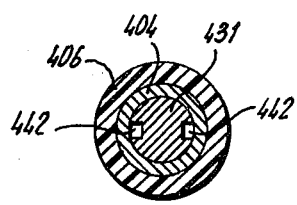

FLOW REGULATOR

The present invention relates to presettable flow-regulators. The invention is particularly useful in apparatus for administering liquids to the body, and is therefore described below with respect to that application, but it will be appreciated that the invention could advantageously be used in other applications as well.

There are many occasions where liquids, such as blood, saline solution, glucose, or water, must be administered to the body at a precise and presettable rate. A number of flow-regulators have been proposed for this purpose, such as pinch-valves, but the known regulators have not proved satisfactory with respect to the precision and convenience of presetting, compactness of the unit, and/or cost of manufacture.

An object of the present invention is to provide a flow-regulator which has advantages in the above respect and which is particularly useful in apparatus for administering liquids to the body.

According to the present invention, there is provided a presettable flow-regulator connectable between two fluid-carrying tubes, comprising: a core connectable at one end to one fluid tube and having a passageway for conducting the fluid therefrom to the outer surface of the core; a flexible sleeve having an open end receivable over said core and connectable at its opposite end to the other fluid tube; said core having an outer diameter slightly smaller than the inner diameter of the flexible sleeve and having a recess of varying cross-section formed in its outer surface and progressing axially of the core; and a ring having an inner diameter slightly smaller than the outer diameter of the flexible sleeve and receivable thereover, said ring being presettable along the length of the flexible sleeve to press the underlying portion thereof against the core at a selected cross-section of said recess to thereby regulate the flow of the fluid between the core and the flexible sleeve from one tube to the other.

In the preferred embodiment of the invention described below, the recess formed on the outer surface of the core is of helical configuration.

Further features and advantages of the invention will be apparent from the description below.

The invention is herein described, by way of example only, with respect to a preferred embodiment illustrated in the drawings, wherein:

FIG. 1 is a longitudinal sectional view of one form of presettable flow-regulator constructed in accordance with the invention;

FIGS. 1a and 1b are enlarged fragmentary views at portions "A" and "B" of FIG. 1;

FIG. 2 is a view corresponding to that of FIG. 1 but showing the presettable ring preset to a specific location to produce a desired rate of flow;

FIG. 3 is an end view of the presettable ring used in the flow-regulator of FIG. 1;

FIG. 4 is a fragmentary view of the inlet end of the FIG. 1 flow-regulator modified to incorporate a drip-chamber therein;

FIG. 5 is a fragmentary view of the outlet end of the FIG. 1 flow-regulator modified to provide an injection site perforatable by a syringe needle for introducing a substance into the fluid flowing through the regulator;

FIG. 6 is a longitudinal sectional view illustrating a modified ring that may be used in the flow-regulator of FIG. 1;

FIG. 7 is a transverse sectional view illustrating a further modification in the ring;

FIG. 8 is a fragmentary longitudinal sectional view illustrating a further modification in the flow-regulator of FIG. 1; and FIG. 9 is a transverse sectional view along lines IX—IX of FIG. 8.

The flow-regulator illustrated in the drawings is particularly for use in apparatus for administering liquids (e.g., blood or saline solution) to the body. It includes but three elements, namely: a core, generally designated 2; an outer flexible sleeve, generally designated 4; and a split-ring 6 presettable along the outer surface of sleeve for presetting the rate of flow of the fluid through the device.

More particularly, core 2 includes an elongated cylindrical section 21 of plastics material formed at one end with a hollow stem 22 for receiving a fluid inlet tube (not shown), the inlet tube being limited by one side of a circular end wall 23. The opposite side of wall 23 is formed with an annular recess 24 for receiving the outer flexible sleeve 4, and with a further annular recess 25 of smaller diameter than that of recess 24 to define an annular chamber 26 between it and the inner surface of the flexible sleeve 4. An axial bore 27 extends through stem 22 and joins with a radial bore 28 to provide a passageway for the flow of fluid from the inlet tube into annular chamber 26.

The main section 21 of core 2 is of smaller outer diameter than the inner diameter of flexible sleeve 4 so as to provide a passageway 29 communicating with chamber 26. In addition, the outer surface of core section 21 is formed with a helical recess 30 progressing axially of the core and of decreasing cross-section from the inlet end (left) of the core to its opposite end.

The decreasing cross-section of the helical recess is particularly illustrated in the exaggerated fragmentary views of FIGS. 1a and 1b, wherein it will be seen that portion 30a (FIG. 1a) of the recess which is closer to the inlet end of the regulator is both deeper and wider than portion 30b (FIG. 1b) of the recess which is closer to the outlet end of the regulator. The helical recess terminates short of the latter end of the core so that the end 31 is smooth and unrecessed.

Flexible sleeve 4 is received at one end in the annular recess 24 of the core 2. The opposite end of the sleeve is reduced in diameter to define a hollow stem 42 for receiving the outlet tube (not shown).

Ring 6 is of flexible plastics material and is formed with an axial split 62 (FIG. 3) to increase its flexibility. In its normal condition, its inner diameter is slightly less than the outer diameter of the flexible sleeve 4, as shown in FIG. 1, so that the ring may be preset along the length of the flexible sleeve to press or pinch the underlying portion thereof against the core section 30, as shown in FIG. 2.

The flow-regulator illustrated in FIGS. 1–3 is used in the following manner:

Stem 22 at the inlet end of core 2 is inserted into the inlet tube, and stem 42 at the opposite end of the flexible sleeve 4 is inserted into the outlet tube, neither of which tubes is illustrated in the drawings. The fluid from the inlet tube thus flows, via bores 27 and 28, to the annular chamber 26 within the flexible sleeve 4, then through the space 29 between the outer surface of the core and the inner surface of the sleeve, and finally out through stem 42 to the outlet tube.

Split-ring 6 may be preset along the outer surface of the flexible sleeve 4 to press or pinch a selected portion thereof against the core, as shown in FIG. 2. The fluid flowing through space 29 is thus forced, where the sleeve is pinched against the core, to flow through the helical recess 30 to pass from one side to the opposite side of ring 6. The cross-section of this passageway depends on the location of the split-ring, and therefore the ring may be preset to any selected position to fix the desired rate of flow. Thus, if the split-ring is moved to the location illustrated in FIG. 1a wherein the respective section 30a of recess 30 is of large cross-section, a large rate of flow will be produced, and if the ring is positioned to the location illustrated in FIG. 1b, a smaller rate of flow will be produced. The ring could also be preset to overlie the non-recessed end 31 of the core, whereupon the flow will be terminated.

If desired, the outer surface of flexible sleeve 4 may be provided with graduation markings indicating the different rates of flow at the different positions of the split-ring.

It will be appreciated that the metering recess 30 may take different shapes and configurations. For example, it may take the form of a single, or a plurality, of recesses extending parallel to the longitudinal axis of the core. The varying cross-section of the recess could be linear or non-linear, or even stepped, to provide for linear, non-linear, or stepped variation of the fluid flow in accordance with the preset position of the split-ring.

FIG. 4 illustrates a modification in the flow-regulator of FIG. 1, wherein the inlet end of the core is modified to incorporate a drip chamber. Thus, the end wall 123, carrying the inlet stem 122 for connection to the inlet tube (not shown), is formed an annular recess 134 receiving one end of a transparent cylindrical wall 135. The opposite end of wall 135 is formed with an annular recess 124 receiving the open end of the flexible sleeve 104, and with the further annular recess 125 defining with the flexible sleeve the annular chamber 126 for the fluid flowing from the inlet tube to the outer face of the core, as in the embodiment of FIGS. 1–3. In the modification of FIG. 4, however, the provision of the outer transparent cylindrical wall 135 provides a viewable drip chamber 136 for the inletted fluid. The fluid is inletted into the drip chamber 136 via axial bore 127 in stem 122, and exits from that chamber into the annular chamber 126 via axial bore 137 and radial bore 128. In all other respects, the device of FIG. 4 is constructed and operates as described above with respect to FIGS. 1–3.

FIG. 5 illustrates a still further possible variation, wherein the end of flexible sleeve 104 having the stem 142 for connection to the outlet tube, is formed with a thickened wall 144 to provide an injection site perforatable by a syringe needle for injecting a substance (e.g. a drug) into the fluid being introduced into the patient's body.

Instead of using a split-ring for ring 6, the ring could be made of resilient material, for example sponge rubber. In addition, the inner face of the ring could be formed with ribs. The latter modification is illustrated in FIG. 6 showing a ring 206 whose inner face includes ribs 207 extending circumferentially (e.g. annularly or spirally) around the ring, and in FIG. 7 showing a ring 306 whose inner face is formed with ribs 307 extending axially of the ring.

The foregoing modifications increase the slidability of the ring with respect to the outer flexible sleeve. To further increase the slidability of the ring, a lubricant may be added. This lubricant would be retained within the sponge rubber of the ring, if such a material is used for the ring, or between the ribs on the inner face of the ring if a ribbed construction is used. Such constructions not only increase the slidability of the ring with respect to the flexible sleeve, but also better accommodate a non-perfect circular section of the core, and thereby reduce the need for close manufacturing tolerances to be following in producing the core.

A further modification that may be included in the flow-regulator is illustrated in FIGS. 8 and 9. In this modification, the core, therein designated as 402, is formed with an annular recess 440 adjacent to the outlet end of the regulator, thereby defining a plug 431 at the outlet end. Plug 431 is formed of a diameter at least equal to, but preferably slightly greater than, that of the remainder of the core 402, in addition, it is provided with a passageway, in the form of a pair of axial recesses 442, having a total cross-sectional area greater than the largest cross-sectional area of the recess 430.

The feature illustrated in FIGS. 8 and 9 enables the flow-regulator to be manipulated to provide an extra large flow of the fluid, if such should be desired in any particular application. Thus, to provide the extra large flow, ring 406 is moved to overlie plug 431. Since the plug is preferably of larger diameter than the remainder of core 402, ring 406 firmly grips sleeve 404 between it and plug 431. The ring 406, together with the underlying portion of the sleeve 404, may be moved slightly in the reverse direction (leftwardly in FIG. 8). Since the ring still grips the underlying portion of sleeve 404 between it and plug 431, a slight contraction is produced in the axial length of sleeve 404, which in turn causes a slight radial enlargement of the sleeve. Accordingly, the annular passageway 429 between core 402 and sleeve 404 is enlarged, thereby permitting an extra large flow of the fluid through the passageway and then through the axial recesses 442.

To facilitate the manufacture of the parts, the sleeve and the core may both have a slightly conical section.

In addition, while the device has been described with respect to a presettable flow-regulator for use in apparatus for administering liquids to the body, it will be appreciated that it could be used in many other applications requiring the precise regulation of a fluid (liquid or gas).

I claim:

1. A presettable flow-regulator connectable between two fluid-carrying tubes, comprising: a core connectable at one end to one fluid tube and having a passageway for conducting the fluid therefrom to the outer surface of the core; a flexible sleeve having an open end receivable over said core and connectable at its opposite end to the other fluid tube; said core having an outer diameter slightly smaller than the inner diameter of the flexible sleeve and having a recess of varying cross-section formed in its outer surface and progressing axially of the core; and a ring having an inner diameter slightly smaller than the outer diameter of the flexible sleeve and receivable thereover, said ring being presettable along the length of the flexible sleeve to press the underlying portion thereof against the core at a selected cross-section of said recess to thereby regulate the flow of the fluid between the core and the flexible sleeve from one tube to the other.

2. A flow-regulator according to claim 1, wherein said recess formed in the outer surface of the core is of helical configuration.

3. A flow-regulator according to claim 1 wherein said recess formed in the outer surface of the core is of decreasing cross-section from said one end of the core to the opposite end thereof.

4. A flow-regulator according to claim 1 wherein said recess terminates short of the end of the core opposite to said one end thereof.

5. A flow-regulator according to claim 1 wherein said presettable ring is a flexible split-ring.

6. A flow-regulator according to claim 1 wherein said one end of the core is formed with a stem for receiving one of the tubes, a first annular recess for receiving the end of the flexible sleeve, a second annular recess of smaller diameter than the first annular recess to define an annular chamber communicating with the space between the core and the flexible sleeve, and a passageway leading from the interior of said stem to said annular chamber.

7. A flow-regulator according to claim 6, wherein said one end of the core includes a circular end wall formed on one side with said stem.

8. A flow-regulator according to claim 7, wherein the opposite side of said circular end wall is formed with said annular recesses.

9. A flow-regulator according to claim 7, wherein the opposite side of said circular end wall includes a transparent cylindrical wall defining therewith a transparent drip chamber.

10. A flow-regulator according to claim 1 wherein said opposite end of the flexible sleeve is formed with a hollow stem for receiving the other tube, and with a thickened wall adjacent to said hollow stem adapted to be perforated by a syringe needle for introducing a substance into the fluid flowing through the regulator.

11. A flow-regulator according to claim 1 wherein said ring is a closed ring and is made of elastic material.

12. A flow-regulator according to claim 11, wherein said elastic material is sponge rubber.

13. A flow-regulator according to claim 1 wherein the inner face of said ring is formed with ribs.

14. A flow-regulator according to claim 13, wherein said ribs on the inner face of the ring extend circumferentially around the ring.

15. A flow-regulator according to claim 13, wherein said ribs on the inner face of the ring extend axially of the ring.

16. A flow-regulator according to claim 13, wherein said ribs on the inner face of the ring extend along a helical line.

17. A flow-regulator according to claim 1 further including a lubricant between the ring and the flexible sleeve.

18. A flow-regulator according to claim 1 wherein said core is formed with an annular recess adjacent to the outlet end of the regulator, said annular recess defining the plug at said outlet end, said plug having a diameter at least equal to that of the remainder of the core and being formed with at least one recess extending axially thereof and having a total cross-sectional area greater than that of said recess of varying cross-section.

* * * * *